(12) United States Patent
McCabe

(10) Patent No.: US 8,663,411 B2
(45) Date of Patent: Mar. 4, 2014

(54) APPARATUS AND METHOD FOR FORMING A PANT-TYPE DIAPER WITH REFASTENABLE SIDE SEAMS

(75) Inventor: John A. McCabe, Sheboygan Falls, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 0 days.

(21) Appl. No.: 13/154,039

(22) Filed: Jun. 6, 2011

(65) Prior Publication Data

US 2011/0297294 A1 Dec. 8, 2011

Related U.S. Application Data

(60) Provisional application No. 61/397,093, filed on Jun. 7, 2010.

(51) Int. Cl.
*A41H 37/02* (2006.01)

(52) U.S. Cl.
USPC .............................................. 156/66; 156/264

(58) Field of Classification Search
USPC .................................... 156/66, 264
See application file for complete search history.

(56) References Cited

U.S. PATENT DOCUMENTS

| | | | |
|---|---|---|---|
| 135,145 A | 1/1873 | Murphy | |
| 293,353 A | 2/1884 | Purvis | |
| 312,257 A | 2/1885 | Cotton et al. | |
| 410,123 A | 8/1889 | Stilwell | |
| 432,742 A | 7/1890 | Stanley | |
| 643,821 A | 2/1900 | Howlett | |
| 1,393,524 A | 10/1921 | Grupe | |
| 1,431,315 A | 10/1922 | Le Moine | |
| 1,605,842 A | 11/1926 | Jones | |
| 1,686,595 A | 10/1928 | Belluche | |
| 1,957,651 A | 5/1934 | Joa | |
| 2,009,857 A | 7/1935 | Potdevin | |
| 2,054,832 A | 9/1936 | Potdevin | |
| 2,117,432 A | 5/1938 | Linscott | |
| 2,128,746 A | 8/1938 | Joa | |
| 2,131,808 A | 10/1938 | Joa | |
| 2,164,408 A | 7/1939 | Joa | |
| 2,167,179 A | 7/1939 | Joa | |
| 2,171,741 A | 9/1939 | Cohn et al. | |
| 2,213,431 A | 9/1940 | Joa | |
| 2,254,290 A | 9/1941 | Joa | |
| 2,254,291 A | 9/1941 | Joa | |
| 2,282,477 A | 5/1942 | Joa | |
| 2,286,096 A | 6/1942 | Joa | |
| 2,296,931 A | 9/1942 | Joa | |
| 2,304,571 A | 12/1942 | Joa | |
| 2,324,930 A | 7/1943 | Joa | |

(Continued)

FOREIGN PATENT DOCUMENTS

BE 1007854 11/1995
CA 1146129 5/1983

(Continued)

*Primary Examiner* — Christopher Schatz
*Assistant Examiner* — John Blades
(74) *Attorney, Agent, or Firm* — Ryan Kromholz & Manion, S.C.

(57) ABSTRACT

A pants type disposable undergarment is provided which is equipped with a pre-fastened pull-on pant with a side lap seam formed by the methods of the present invention, and methods for producing such disposable undergarments.

1 Claim, 12 Drawing Sheets

(56) References Cited

U.S. PATENT DOCUMENTS

| | | |
|---|---|---|
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,627,859 A | 2/1953 | Hargrave |
| 2,695,025 A | 11/1954 | Andrews |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,788,786 A | 4/1957 | Dexter |
| 2,811,905 A | 11/1957 | Kennedy, Jr. |
| 2,828,745 A | 4/1958 | Deutz |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,890,700 A | 6/1959 | Lonberg-Holm |
| 2,913,862 A | 11/1959 | Sabee |
| 2,939,461 A | 6/1960 | Joa |
| 2,939,646 A | 6/1960 | Stone |
| 2,960,143 A | 11/1960 | Joa |
| 2,990,081 A | 6/1961 | De Neui et al. |
| 2,991,739 A | 7/1961 | Joa |
| 3,016,207 A | 1/1962 | Comstock, III |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,089,494 A | 5/1963 | Schwartz |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,318,608 A | 5/1967 | Smrekar |
| 3,322,589 A | 5/1967 | Joa |
| 3,342,184 A | 9/1967 | Joa |
| 3,356,092 A | 12/1967 | Joa |
| 3,360,103 A | 12/1967 | Joa |
| 3,336,847 A | 1/1968 | Johnson |
| 3,391,777 A | 7/1968 | Joa |
| 3,454,442 A | 7/1969 | Heller, Jr. |
| 3,463,413 A | 8/1969 | Smith |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger et al. |
| 3,728,191 A | 4/1973 | Wierzba et al. |
| 3,751,224 A | 8/1973 | Wackerle |
| 3,758,102 A | 9/1973 | Munn et al. |
| 3,772,120 A | 11/1973 | Radzins |
| 3,776,798 A | 12/1973 | Milano |
| 3,796,360 A | 3/1974 | Alexeff |
| 3,811,987 A | 5/1974 | Wilkinson et al. |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,901,238 A | 8/1975 | Gellert et al. |
| 3,903,768 A | 9/1975 | Amberg et al. |
| 3,904,147 A | 9/1975 | Taitel et al. |
| 3,918,698 A | 11/1975 | Coast |
| 3,960,646 A | 6/1976 | Wiedamann |
| 3,988,194 A | 10/1976 | Babcock et al. |
| 3,991,994 A | 11/1976 | Farish |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,325,519 A | 4/1982 | McLean |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,543,152 A | 9/1985 | Nozaka |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,608,115 A | 8/1986 | Schroth et al. |
| 4,610,681 A | 9/1986 | Strohbeen et al. |
| 4,610,682 A | 9/1986 | Kopp |
| 4,614,076 A | 9/1986 | Rathemacher |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |

(56) References Cited

U.S. PATENT DOCUMENTS

| | | |
|---|---|---|
| 4,663,220 A | 5/1987 | Wisneski et al. |
| 4,672,705 A | 6/1987 | Bors et al. |
| 4,675,016 A | 6/1987 | Meuli et al. |
| 4,675,062 A | 6/1987 | Instance |
| 4,675,068 A | 6/1987 | Lundmark |
| 4,686,136 A | 8/1987 | Homonoff et al. |
| 4,693,056 A | 9/1987 | Raszewski |
| 4,701,239 A | 10/1987 | Craig |
| 4,720,415 A | 1/1988 | Vander Vielen et al. |
| 4,723,698 A | 2/1988 | Schoonderbeek |
| 4,726,874 A | 2/1988 | Van Vliet |
| 4,726,876 A | 2/1988 | Tomsovic, Jr. |
| 4,743,241 A | 5/1988 | Igaue et al. |
| 4,751,997 A | 6/1988 | Hirsch |
| 4,753,429 A | 6/1988 | Irvine et al. |
| 4,756,141 A | 7/1988 | Hirsch et al. |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,782,647 A | 11/1988 | Williams et al. |
| 4,785,986 A | 11/1988 | Daane et al. |
| 4,795,510 A | 1/1989 | Wittrock et al. |
| 4,798,353 A | 1/1989 | Peugh |
| 4,801,345 A | 1/1989 | Dussaud et al. |
| 4,802,570 A | 2/1989 | Hirsch et al. |
| 4,840,609 A | 6/1989 | Jones et al. |
| 4,845,964 A | 7/1989 | Bors et al. |
| 4,864,802 A | 9/1989 | D'Angelo |
| 4,880,102 A | 11/1989 | Indrebo |
| 4,888,231 A | 12/1989 | Angstadt |
| 4,892,536 A | 1/1990 | Des Marais et al. |
| 4,904,440 A | 2/1990 | Angstadt |
| 4,908,175 A | 3/1990 | Angstadt |
| 4,909,019 A | 3/1990 | Delacretaz et al. |
| 4,915,767 A | 4/1990 | Rajala et al. |
| 4,917,746 A | 4/1990 | Kons |
| 4,925,520 A | 5/1990 | Beaudoin et al. |
| 4,927,322 A | 5/1990 | Schweizer et al. |
| 4,927,486 A | 5/1990 | Fattal et al. |
| 4,927,582 A | 5/1990 | Bryson |
| 4,937,887 A | 7/1990 | Schreiner |
| 4,963,072 A | 10/1990 | Miley et al. |
| 4,987,940 A | 1/1991 | Straub et al. |
| 4,994,010 A | 2/1991 | Doderer-Winkler |
| 5,000,806 A | 3/1991 | Merkatoris et al. |
| 5,021,111 A | 6/1991 | Swenson |
| 5,025,910 A | 6/1991 | Lasure et al. |
| 5,045,039 A | 9/1991 | Bay |
| 5,062,597 A | 11/1991 | Martin et al. |
| 5,064,179 A | 11/1991 | Martin |
| 5,064,492 A | 11/1991 | Friesch |
| 5,080,741 A | 1/1992 | Nomura et al. |
| 5,094,658 A | 3/1992 | Smithe et al. |
| 5,096,532 A | 3/1992 | Neuwirth et al. |
| 5,108,017 A | 4/1992 | Adamski, Jr. et al. |
| 5,109,767 A | 5/1992 | Nyfeler et al. |
| 5,110,403 A | 5/1992 | Ehlert |
| 5,127,981 A | 7/1992 | Straub et al. |
| 5,131,525 A | 7/1992 | Musschoot |
| 5,131,901 A | 7/1992 | Moll |
| 5,133,511 A | 7/1992 | Mack |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,190,234 A | 3/1993 | Ezekiel |
| 5,195,684 A | 3/1993 | Radzins |
| 5,203,043 A | 4/1993 | Riedel |
| 5,213,645 A | 5/1993 | Nomura et al. |
| 5,222,422 A | 6/1993 | Benner, Jr. et al. |
| 5,223,069 A | 6/1993 | Tokuno et al. |
| 5,226,992 A | 7/1993 | Morman |
| 5,246,433 A | 9/1993 | Hasse et al. |
| 5,252,228 A | 10/1993 | Stokes |
| 5,267,933 A | 12/1993 | Precoma |
| 5,273,228 A | 12/1993 | Yoshida |
| 5,275,676 A | 1/1994 | Rooyakkers et al. |
| 5,308,345 A | 5/1994 | Herrin |
| 5,328,438 A | 7/1994 | Crowley |
| 5,340,424 A | 8/1994 | Matsushita |
| 5,368,893 A | 11/1994 | Sommer et al. |
| 5,389,173 A | 2/1995 | Merkatoris et al. |
| 5,393,360 A | 2/1995 | Bridges et al. |
| 5,407,507 A | 4/1995 | Ball |
| 5,407,513 A | 4/1995 | Hayden et al. |
| 5,415,649 A | 5/1995 | Watanabe et al. |
| 5,421,924 A | 6/1995 | Ziegelhoffer et al. |
| 5,424,025 A | 6/1995 | Hanschen et al. |
| 5,429,576 A | 7/1995 | Doderer-Winkler |
| 5,435,802 A | 7/1995 | Kober |
| 5,449,353 A | 9/1995 | Watanabe et al. |
| 5,464,401 A | 11/1995 | Hasse et al. |
| 5,486,253 A | 1/1996 | Otruba |
| 5,494,622 A | 2/1996 | Heath et al. |
| 5,500,075 A | 3/1996 | Herrmann |
| 5,516,392 A | 5/1996 | Bridges et al. |
| 5,518,566 A | 5/1996 | Bridges et al. |
| 5,525,175 A | 6/1996 | Blenke et al. |
| 5,531,850 A | 7/1996 | Herrmann |
| 5,540,647 A | 7/1996 | Weiermann et al. |
| 5,545,275 A | 8/1996 | Herrin et al. |
| 5,545,285 A | 8/1996 | Johnson |
| 5,552,013 A | 9/1996 | Ehlert et al. |
| 5,556,360 A | 9/1996 | Kober et al. |
| 5,556,504 A | 9/1996 | Rajala et al. |
| 5,560,793 A | 10/1996 | Ruscher et al. |
| 5,575,187 A | 11/1996 | Dieterlen |
| 5,586,964 A | 12/1996 | Chase |
| 5,602,747 A | 2/1997 | Rajala |
| 5,603,794 A | 2/1997 | Thomas |
| 5,624,420 A | 4/1997 | Bridges et al. |
| 5,624,428 A | 4/1997 | Sauer |
| 5,628,738 A | 5/1997 | Suekane |
| 5,634,917 A | 6/1997 | Fujioka et al. |
| 5,643,165 A | 7/1997 | Klekamp |
| 5,643,396 A | 7/1997 | Rajala et al. |
| 5,645,543 A | 7/1997 | Nomura et al. |
| 5,659,229 A | 8/1997 | Rajala |
| 5,660,657 A | 8/1997 | Rajala et al. |
| 5,660,665 A | 8/1997 | Jalonen |
| 5,683,376 A | 11/1997 | Kato et al. |
| 5,683,531 A | 11/1997 | Roessler et al. |
| RE35,687 E | 12/1997 | Igaue et al. |
| 5,693,165 A | 12/1997 | Schmitz |
| 5,699,653 A | 12/1997 | Hartman et al. |
| 5,705,013 A | 1/1998 | Nease |
| 5,707,470 A | 1/1998 | Rajala et al. |
| 5,711,832 A | 1/1998 | Glaug et al. |
| 5,725,518 A | 3/1998 | Coates |
| 5,725,714 A | 3/1998 | Fujioka |
| 5,743,994 A | 4/1998 | Roessler et al. |
| 5,745,922 A | 5/1998 | Rajala et al. |
| 5,746,869 A | 5/1998 | Hayden et al. |
| 5,749,989 A | 5/1998 | Linman et al. |
| 5,766,389 A | 6/1998 | Brandon et al. |
| 5,788,797 A | 8/1998 | Herrin et al. |
| 5,817,199 A | 10/1998 | Brennecke et al. |
| 5,829,164 A | 11/1998 | Kotitschke |
| 5,836,931 A | 11/1998 | Toyoda et al. |
| 5,858,012 A | 1/1999 | Yamaki et al. |
| 5,865,393 A | 2/1999 | Kreft et al. |
| 5,868,727 A | 2/1999 | Barr et al. |
| 5,876,027 A | 3/1999 | Fukui et al. |
| 5,876,792 A | 3/1999 | Caldwell |
| 5,879,500 A | 3/1999 | Herrin et al. |
| 5,902,431 A | 5/1999 | Wilkinson et al. |
| 5,932,039 A | 8/1999 | Popp et al. |
| 5,938,193 A | 8/1999 | Bluemle et al. |
| 5,964,390 A | 10/1999 | Borresen et al. |
| 5,964,970 A | 10/1999 | Woolwine et al. |
| 6,022,443 A | 2/2000 | Rajala et al. |

(56) References Cited

U.S. PATENT DOCUMENTS

| | | |
|---|---|---|
| 6,036,805 A | 3/2000 | McNichols |
| 6,043,836 A | 3/2000 | Kerr et al. |
| 6,050,517 A | 4/2000 | Dobrescu et al. |
| 6,074,110 A | 6/2000 | Verlinden et al. |
| 6,076,442 A | 6/2000 | Arterburn et al. |
| 6,098,249 A | 8/2000 | Toney et al. |
| 6,123,792 A | 9/2000 | Samida et al. |
| 6,171,432 B1 | 1/2001 | Brisebois |
| 6,183,576 B1 | 2/2001 | Couillard et al. |
| 6,195,850 B1 | 3/2001 | Melbye |
| 6,210,386 B1 | 4/2001 | Inoue |
| 6,212,859 B1 | 4/2001 | Bielik, Jr. et al. |
| 6,214,147 B1 | 4/2001 | Mortellite et al. |
| 6,250,048 B1 | 6/2001 | Linkiewicz |
| 6,264,784 B1 | 7/2001 | Menard et al. |
| 6,276,421 B1 | 8/2001 | Valenti et al. |
| 6,276,587 B1 | 8/2001 | Borresen |
| 6,284,081 B1 | 9/2001 | Vogt et al. |
| 6,287,409 B1 | 9/2001 | Stephany |
| 6,306,122 B1 | 10/2001 | Narawa et al. |
| 6,309,336 B1 | 10/2001 | Muessig et al. |
| 6,312,420 B1 | 11/2001 | Sasaki et al. |
| 6,314,333 B1 | 11/2001 | Rajala et al. |
| 6,315,022 B1 | 11/2001 | Herrin et al. |
| 6,319,347 B1 | 11/2001 | Rajala |
| 6,336,921 B1 | 1/2002 | Kato et al. |
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,431,038 B2 | 8/2002 | Couturier |
| 6,440,246 B1 | 8/2002 | Vogt et al. |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Glaug et al. |
| 6,482,278 B1 | 11/2002 | McCabe et al. |
| 6,494,244 B2 | 12/2002 | Parrish et al. |
| 6,514,233 B1 | 2/2003 | Glaug |
| 6,521,320 B2 | 2/2003 | McCabe et al. |
| 6,523,595 B1 | 2/2003 | Milner et al. |
| 6,524,423 B1 | 2/2003 | Hilt et al. |
| 6,533,879 B2 | 3/2003 | Quereshi et al. |
| 6,540,857 B1 | 4/2003 | Coenen et al. |
| 6,547,909 B1 | 4/2003 | Butterworth |
| 6,551,228 B1 | 4/2003 | Richards |
| 6,551,430 B1 | 4/2003 | Glaug et al. |
| 6,554,815 B1 | 4/2003 | Umebayashi |
| 6,569,275 B1 | 5/2003 | Popp et al. |
| 6,572,520 B2 | 6/2003 | Blumle |
| 6,581,517 B1 | 6/2003 | Becker et al. |
| 6,585,841 B1 | 7/2003 | Popp et al. |
| 6,589,149 B1 | 7/2003 | VanEperen et al. |
| 6,596,107 B2 | 7/2003 | Stopher |
| 6,596,108 B2 | 7/2003 | McCabe |
| 6,605,172 B1 | 8/2003 | Anderson et al. |
| 6,605,173 B2 | 8/2003 | Glaug et al. |
| 6,637,583 B1 | 10/2003 | Andersson |
| 6,648,122 B1 | 11/2003 | Hirsch et al. |
| 6,649,010 B2 | 11/2003 | Parrish et al. |
| 6,656,309 B1 | 12/2003 | Parker et al. |
| 6,659,150 B1 | 12/2003 | Perkins et al. |
| 6,659,991 B2 | 12/2003 | Suckane |
| 6,675,552 B2 | 1/2004 | Kunz et al. |
| 6,684,925 B2 | 2/2004 | Nagate et al. |
| 6,722,494 B2 | 4/2004 | Nakakado |
| 6,730,189 B1 | 5/2004 | Franzmann |
| 6,743,324 B2 | 6/2004 | Hargett et al. |
| 6,750,466 B2 | 6/2004 | Song |
| 6,758,109 B2 | 7/2004 | Nakakado |
| 6,766,817 B2 | 7/2004 | da Silva |
| 6,808,582 B2 | 10/2004 | Popp et al. |
| D497,991 S | 11/2004 | Otsubo et al. |
| 6,814,217 B2 | 11/2004 | Blumenthal et al. |
| 6,820,671 B2 | 11/2004 | Calvert |
| 6,837,840 B2 | 1/2005 | Yonekawa et al. |
| 6,840,616 B2 | 1/2005 | Summers |
| 6,852,186 B1 | 2/2005 | Matsuda et al. |
| 6,875,202 B2 | 4/2005 | Kumasaka et al. |
| 6,893,528 B2 | 5/2005 | Middelstadt et al. |
| 6,913,718 B2 | 7/2005 | Ducker |
| 6,918,404 B2 | 7/2005 | Dias da Silva |
| 6,976,521 B2 | 12/2005 | Mlinar |
| 6,978,486 B2 | 12/2005 | Zhou et al. |
| 7,017,820 B1 | 3/2006 | Brunner |
| 7,045,031 B2 | 5/2006 | Popp et al. |
| 7,066,586 B2 | 6/2006 | da Silva |
| 7,077,393 B2 | 7/2006 | Ishida |
| 7,130,710 B2 | 10/2006 | Schechtman |
| 7,172,666 B2 | 2/2007 | Groves et al. |
| 7,195,684 B2 | 3/2007 | Satoh |
| 7,201,345 B2 | 4/2007 | Werner |
| 7,214,174 B2 | 5/2007 | Allen et al. |
| 7,214,287 B2 | 5/2007 | Shiomi et al. |
| 7,247,219 B2 | 7/2007 | O'Dowd |
| 7,303,708 B2 | 12/2007 | Andrews et al. |
| 7,380,213 B2 | 5/2008 | Pesin |
| 7,398,870 B2 | 7/2008 | McCabe |
| 7,449,084 B2 | 11/2008 | Nakakado |
| 7,452,436 B2 | 11/2008 | Andrews |
| 7,533,709 B2 | 5/2009 | Meyer |
| 7,537,215 B2 | 5/2009 | Beaudoin et al. |
| 7,587,966 B2 | 9/2009 | Nakakado et al. |
| 7,618,513 B2 | 11/2009 | Meyer |
| 7,638,014 B2 | 12/2009 | Coose et al. |
| 7,640,962 B2 | 1/2010 | Meyer et al. |
| 7,703,599 B2 | 4/2010 | Meyer |
| 7,708,849 B2 | 5/2010 | McCabe |
| 7,770,712 B2 | 8/2010 | McCabe |
| 7,771,407 B2 | 8/2010 | Umebayashi |
| 7,780,052 B2 | 8/2010 | McCabe |
| 7,811,403 B2 | 10/2010 | Andrews |
| 7,861,756 B2 | 1/2011 | Jenquin et al. |
| 7,871,400 B2 | 1/2011 | Sablone et al. |
| 7,909,956 B2 | 3/2011 | Coose et al. |
| 7,975,584 B2 | 7/2011 | McCabe |
| 7,987,964 B2 | 8/2011 | McCabe |
| 8,007,484 B2 | 8/2011 | McCabe et al. |
| 8,007,623 B2 | 8/2011 | Andrews |
| 8,011,493 B2 | 9/2011 | Giuliani et al. |
| 8,016,972 B2 | 9/2011 | Andrews et al. |
| 2001/0012813 A1 | 8/2001 | Bluemle |
| 2001/0017181 A1 | 8/2001 | Otruba et al. |
| 2002/0046802 A1 | 4/2002 | Tachibana et al. |
| 2002/0059013 A1 | 5/2002 | Rajala et al. |
| 2002/0096241 A1 | 7/2002 | Instance |
| 2002/0125105 A1 | 9/2002 | Nakakado |
| 2002/0162776 A1 | 11/2002 | Hergeth |
| 2003/0000620 A1 | 1/2003 | Herrin et al. |
| 2003/0015209 A1 | 1/2003 | Gingras et al. |
| 2003/0051802 A1 | 3/2003 | Hargett et al. |
| 2003/0052148 A1 | 3/2003 | Rajala et al. |
| 2003/0066585 A1 | 4/2003 | McCabe |
| 2003/0083638 A1 | 5/2003 | Molee |
| 2003/0084984 A1 | 5/2003 | Glaug et al. |
| 2003/0089447 A1 | 5/2003 | Molee et al. |
| 2003/0121614 A1 | 7/2003 | Tabor et al. |
| 2003/0135189 A1 | 7/2003 | Umebayashi |
| 2004/0007328 A1 | 1/2004 | Popp et al. |
| 2004/0016500 A1 | 1/2004 | Tachibana et al. |
| 2004/0044325 A1 | 3/2004 | Corneliusson |
| 2004/0087425 A1 | 5/2004 | Ng et al. |
| 2004/0112517 A1 | 6/2004 | Groves et al. |
| 2004/0164482 A1 | 8/2004 | Edinger |
| 2004/0182497 A1 | 9/2004 | Lowrey |
| 2005/0000628 A1 | 1/2005 | Norrby |
| 2005/0022476 A1 | 2/2005 | Hamer |
| 2005/0139713 A1 | 6/2005 | Weber et al. |
| 2005/0196538 A1 | 9/2005 | Sommer et al. |
| 2005/0230056 A1 | 10/2005 | Meyer et al. |
| 2005/0230449 A1 | 10/2005 | Meyer et al. |
| 2005/0233881 A1 | 10/2005 | Meyer |

(56) References Cited

U.S. PATENT DOCUMENTS

| | | |
|---|---|---|
| 2005/0234412 A1 | 10/2005 | Andrews et al. |
| 2005/0257881 A1 | 11/2005 | Coose et al. |
| 2005/0275148 A1 | 12/2005 | Beaudoin et al. |
| 2006/0021300 A1 | 2/2006 | Tada et al. |
| 2006/0137298 A1 | 6/2006 | Oshita et al. |
| 2006/0224137 A1 | 10/2006 | McCabe et al. |
| 2006/0265867 A1 | 11/2006 | Schaap |
| 2007/0074953 A1 | 4/2007 | McCabe |
| 2008/0077418 A1 | 3/2008 | Coleman |
| 2008/0210067 A1* | 9/2008 | Schlinz et al. ............ 83/23 |
| 2008/0223537 A1 | 9/2008 | Wiedmann |
| 2008/0281286 A1* | 11/2008 | Petersen ............ 156/60 |
| 2009/0020211 A1 | 1/2009 | Andrews et al. |
| 2009/0126864 A1* | 5/2009 | Tachibana et al. ............ 156/216 |
| 2010/0078119 A1 | 4/2010 | Yamamoto |
| 2010/0078120 A1 | 4/2010 | Otsubo |
| 2010/0078127 A1 | 4/2010 | Yamamoto |
| 2010/0193138 A1 | 8/2010 | Eckstein |
| 2010/0193155 A1 | 8/2010 | Nakatani |
| 2011/0106042 A1* | 5/2011 | Sablone et al. ......... 604/385.25 |

FOREIGN PATENT DOCUMENTS

| | | |
|---|---|---|
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2404154 | 10/2001 |
| CA | 2541194 | 10/2006 |
| CA | 2559517 | 4/2007 |
| CA | 2337700 | 8/2008 |
| CA | 2407867 | 6/2010 |
| DE | 60123502 | 10/2006 |
| DE | 60216550 | 12/2006 |
| DE | 102005048868 | 4/2007 |
| DE | 102006047280 | 4/2007 |
| EP | 0044206 | 1/1982 |
| EP | 0048011 | 3/1982 |
| EP | 0089106 | 9/1983 |
| EP | 0099732 | 2/1984 |
| EP | 0206208 | 12/1986 |
| EP | 0304140 | 2/1989 |
| EP | 0439897 | 8/1991 |
| EP | 0455231 A1 | 11/1991 |
| EP | 510251 | 10/1992 |
| EP | 0652175 A1 | 5/1995 |
| EP | 0811473 | 12/1997 |
| EP | 0901780 | 3/1999 |
| EP | 0990588 | 4/2000 |
| EP | 1132325 A2 | 9/2001 |
| EP | 1199057 | 4/2002 |
| EP | 1272347 | 1/2003 |
| EP | 1366734 | 12/2003 |
| EP | 1571249 | 9/2005 |
| EP | 1619008 | 1/2006 |
| EP | 1707168 A2 | 10/2006 |
| EP | 1726414 | 11/2006 |
| EP | 1302424 | 12/2006 |
| EP | 1801045 | 6/2007 |
| EP | 1941853 | 7/2008 |
| EP | 2233116 | 9/2010 |
| EP | 2238955 | 10/2010 |
| ES | 509706 | 11/1982 |
| ES | 520559 | 12/1983 |
| ES | 296211 | 12/1987 |
| ES | 200601373 | 7/2009 |
| ES | 2311349 | 9/2009 |
| FR | 2177355 | 11/1973 |
| FR | 2255961 | 7/1975 |
| FR | 1132325 | 10/2006 |
| FR | 2891811 | 4/2007 |
| GB | 191101501 A | 0/1912 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 2045298 | 10/1980 |
| GB | 2115775 | 9/1983 |
| GB | 2288316 | 10/1995 |
| IT | 1374910 | 5/2010 |
| IT | 1374911 | 5/2010 |
| JP | 428364 | 1/1992 |
| JP | 542180 | 2/1993 |
| JP | 576566 | 3/1993 |
| JP | 626160 | 2/1994 |
| JP | 626161 | 2/1994 |
| JP | 6197925 A | 7/1994 |
| JP | 9299398 | 11/1997 |
| JP | 10035621 | 2/1998 |
| JP | 10-277091 A | 10/1998 |
| JP | 2008-161300 * | 7/2008 ............ A61F 13/49 |
| SE | 0602047 | 5/2007 |
| SE | 0601003-7 | 6/2007 |
| SE | 0601145-6 | 10/2009 |
| WO | WO9403301 | 2/1994 |
| WO | WO9732552 | 9/1997 |
| WO | WO9747265 | 12/1997 |
| WO | WO9747810 | 12/1997 |
| WO | WO9821134 | 5/1998 |
| WO | WO9907319 | 2/1999 |
| WO | WO9913813 A1 | 3/1999 |
| WO | WO9932385 | 7/1999 |
| WO | WO9965437 | 12/1999 |
| WO | WO0143682 | 6/2001 |
| WO | WO0172237 A2 | 10/2001 |
| WO | WO2004007329 | 1/2004 |
| WO | WO2005075163 | 8/2005 |
| WO | WO 2007029115 | 3/2007 |
| WO | WO2007039800 | 4/2007 |
| WO | WO 2007039800 | 4/2007 |
| WO | WO 2007/126347 A1 | 11/2007 |
| WO | WO2008001209 | 1/2008 |
| WO | WO 2008155618 | 12/2008 |

* cited by examiner

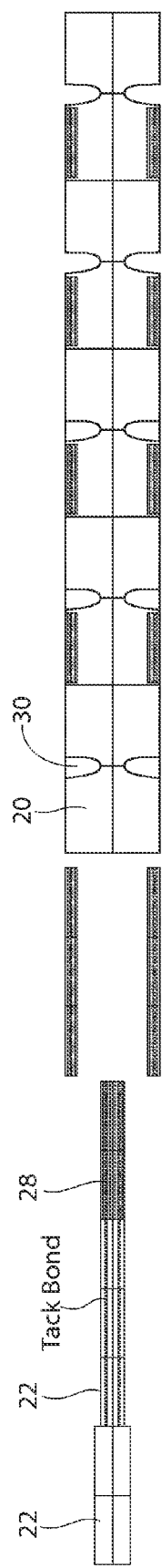
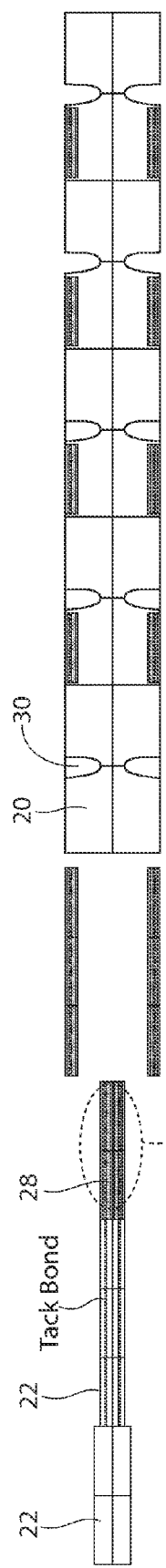
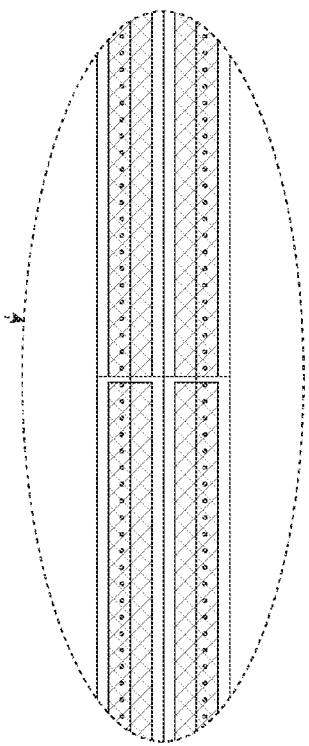

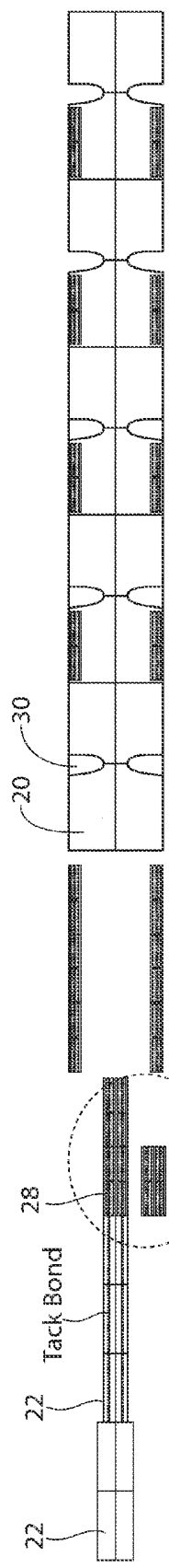
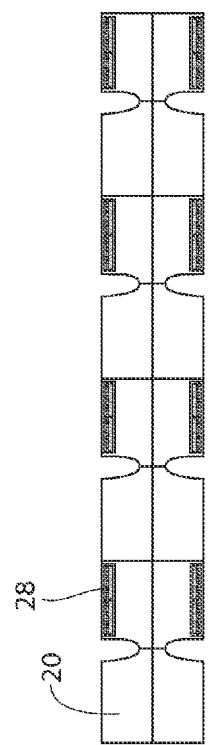
Fig. 17
Fig. 18

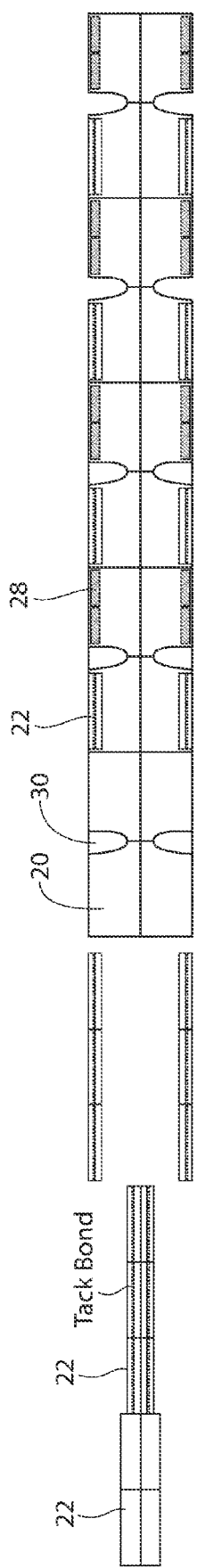
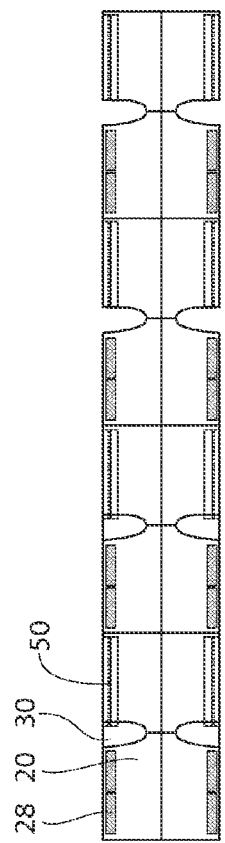

APPARATUS AND METHOD FOR FORMING A PANT-TYPE DIAPER WITH REFASTENABLE SIDE SEAMS

RELATED APPLICATIONS

This application claims the benefit of co-pending U.S. Provisional Patent Application Ser. No. 61/397,093, filed 7 Jun. 2010.

BACKGROUND OF THE INVENTION

The present invention related to disposable undergarments and more particularly, a pants type undergarment which is equipped with refastenable side seams.

Disposable undergarments of the children's training pant type, or of the adult incontinence type, are generally made up of two nonwoven layers of material with elastic strands of material placed between the two nonwoven layers of material thus creating an elastic web laminate.

SUMMARY OF THE INVENTION

The present invention discloses methods of forming a pants type diaper with refastenable side seams. A pants type disposable undergarment is provided which is equipped with a pre-fastened pull-on pant with a side lap seam formed by the methods of the present invention. Top and bottom portions of a side panel assembly are folded over a stretch portion of the side panel, and both the top and bottom portions are bonded to the stretch portion of the side panel, at first temporary bond points and at second ultrasonic or mechanical bond portions. The second ultrasonic or mechanical bond portions are overlain with a hook-type fastener for later bonding with the first temporary bond points, to form a lap seam at the left and right sides of the waist of a wearer. A folded product is produced that is pre-fastened in this manner, but the bond between the hook-type fastener and the first temporary bonded portion can be released and re-fastened if desired.

A product and method to produce a resealable pant such that the front and rear waist side panel regions can be easily engaged with one another.

A method to produce a resealable pant in such a manner so that the front and rear waist side panels are a single piece during manufacturing is disclosed. A hinged panel with a resealable fastener to align with the mating side panel when folded to form a lap seam is also disclosed.

BRIEF DESCRIPTION OF THE DRAWINGS

FIG. 13 is schematic representation of formation of an alternate embodiment of the present invention, disclosed is a nonwoven tab process with a continuous hook formation, with the hooks away from the body.

FIG. 14 is a schematic representation of formation of an alternate embodiment of the present invention, disclosed is a nonwoven tab process with a discrete hook formation, with the hooks away from the body.

FIG. 17 is a schematic representation of formation of an alternate embodiment of the present invention, disclosed is a nonwoven tab process with a multiple discrete hook overlapping cut formation, with the hooks away from the body.

FIG. 18 is a schematic representation of formation of an alternate embodiment of the present invention, disclosed is a nonwoven tab process with hooks on the front side panel, with the hooks away from the body.

FIG. 19 is a schematic representation of formation of an alternate embodiment of the present invention, disclosed is a nonwoven tab process with hooks on the front side panel, and nonwoven tabs on the back panel, with hooks toward the body.

FIG. 20 is a schematic representation of formation of an alternate embodiment of the present invention, disclosed is a nonwoven tab process with hooks on the rear or back side panel, and nonwoven tabs on the front panel, with hooks toward the body.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Referring to the Figures generally, two adjacent products are shown constructed next to one another because the products 10 are preferably constructed on a continuous processing system for later separation to form individual diaper products (see, e.g., FIG. 9 prior to separation to form individual products in FIG. 10).

Figure 1:
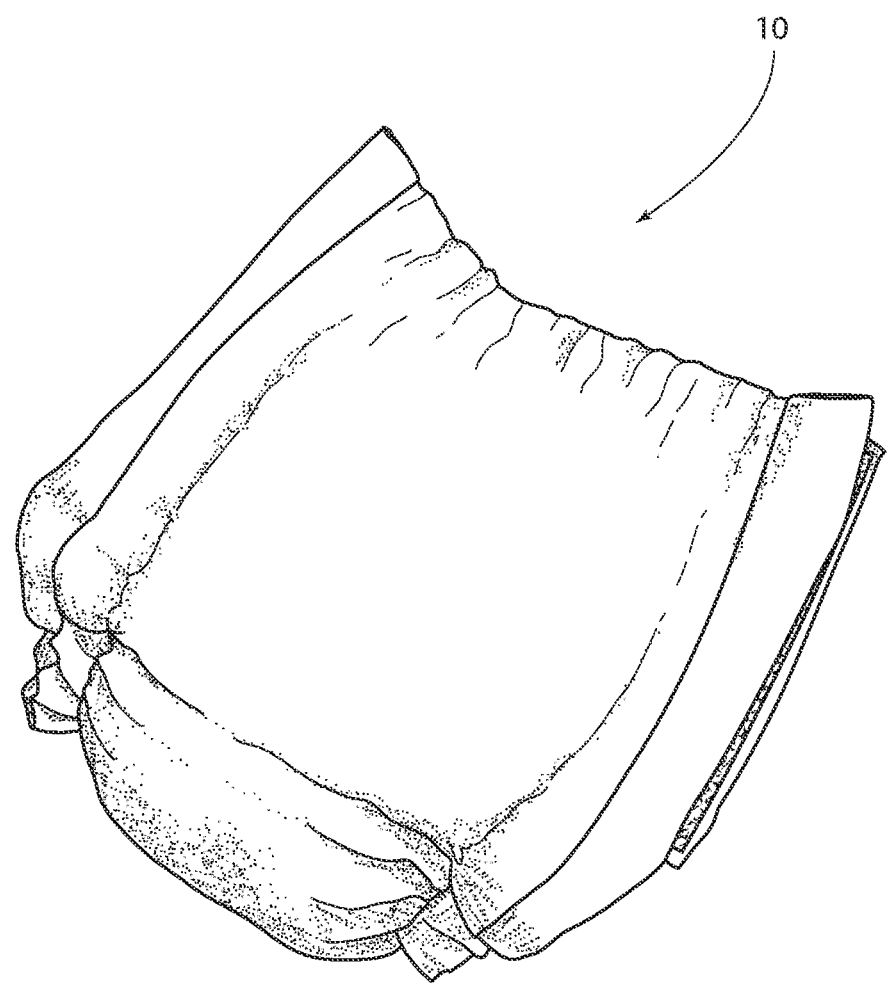
FIG. 1 is a perspective view of an undergarment produced according to the present invention.

FIG. 1 is a perspective view of an undergarment 10 produced according to the present invention.

Figure 2:
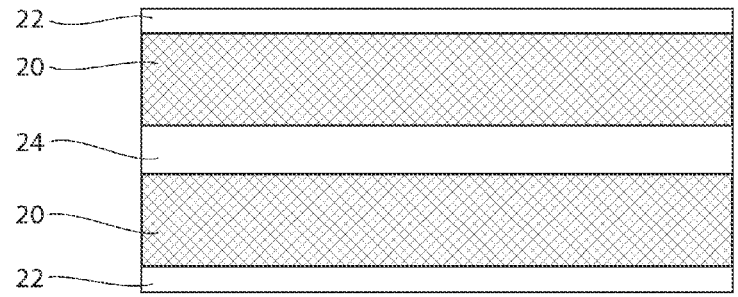
FIG. 2 is a top planar view of a composite of material used to form a side panel.

Referring now to FIG. 2 a top planar view of a composite of material used to form a side panel is shown. First and second segments of material 22 are provided at the top and bottom of the composite, along with first and second segments of preferably stretchy material 20. The first and second segments of material 22 can be formed of the same piece of stretch material 20, or formed separately of stretch or non-stretch material and then bonded to the stretch material 20. A segment of non-stretch material 24 is provided between the first and second segments 20 as shown.

Figure 3:
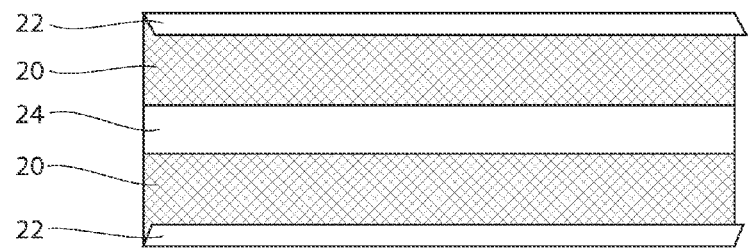
FIG. 3 is a top planar view of a side panel assembly of embodiment shown in FIG. 2, with the top and bottom non-stretch materials folded over.

Referring now to FIG. 3, the first and second segments of material 22 are folded either over or under the adjoining first and second segments of stretch material 22. This can be done with a folding machine known in the art.

Figure 4:
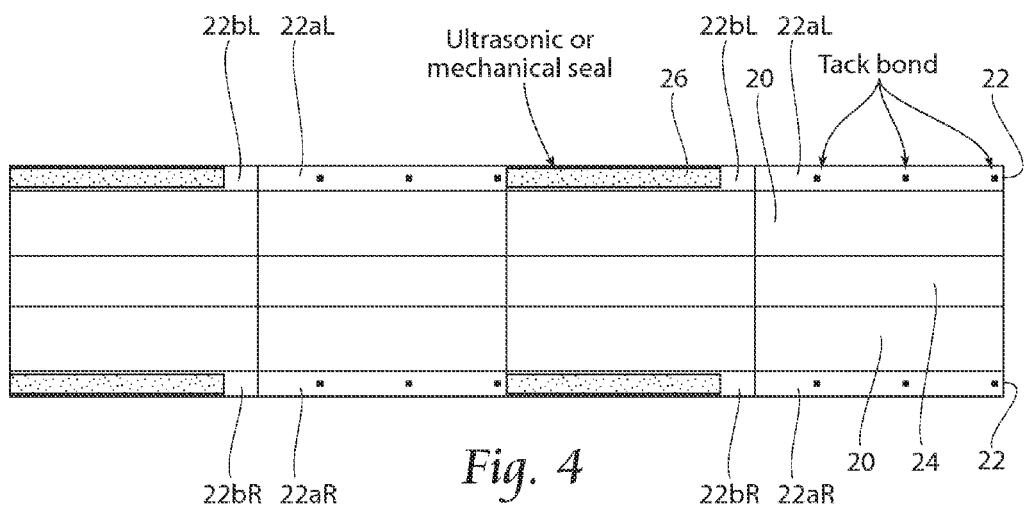
FIG. 4 is a top planar view of assembly of embodiment shown in FIG. 3, with the top and bottom non-stretch materials folded over and bonded in portions to the stretch portions.

As shown in FIG. 4 a top planar view of assembly of embodiment shown in FIG. 3 is shown, with the top and bottom segments of material 22 folded over. The top and bottom segments of material 22 are then conceptually divided into segments 22a and 22b, both at the top and the bottom of the composite, alternating continuously in what will eventually become physically divided portions which will be the front left (top 22aL), front right (bottom 22aR) and the back left (top 22bL) and back right (bottom 22bR) side panel portions.

In areas 22aR and 22aL (front left and right side panel portions), the folded segments of material 22 are temporarily bonded to the underlying (or overlying) layer(s) of stretch material 20. The temporary bonding can be done for instance at spaced apart tack bond sites. The purpose of the temporary bond is to provide control of the material throughout the high-speed manufacturing process, but to allow the bond to become detached when the lap seam is eventually formed, and worn about the waist of a user.

In areas 22bR and 22bL (rear left and right side panel portions), the folded segments of material 22 are ultrasonically or mechanically bonded to the underlying (or overlying) layer(s) of stretch material 20 in zones 26. The bonding can be done in other ways, such as adhesively.

Figure 5:
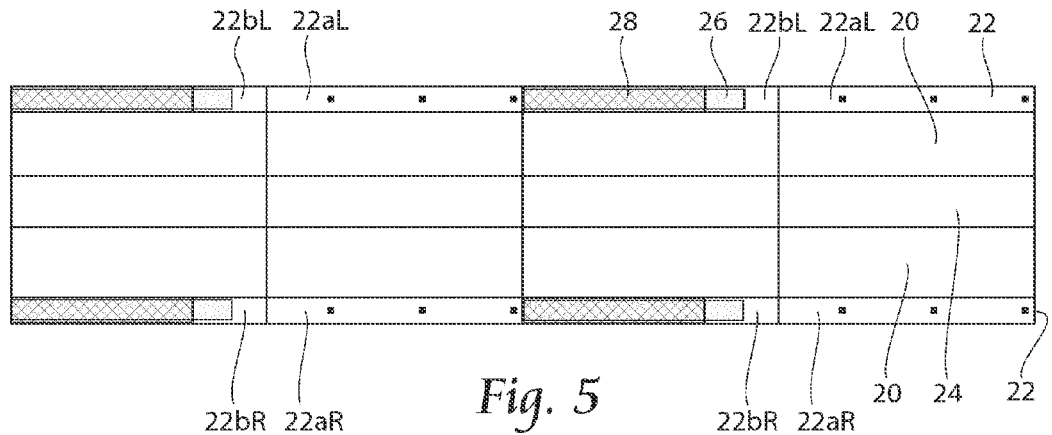
FIG. 5 is a top planar view of assembly of embodiment shown in FIG. 4, with the top and bottom non-stretch materials folded over and bonded in portions to the stretch portions, and a hook material applied to the back side panel proximate to the bond area.

Following this step, and referring now to FIG. 5, after the top and bottom materials 22 have been folded over and bonded in portions to the stretch portions 20 as previously described, a material 28 is applied to the back side panel in areas 22bL and 22bR proximate to and preferably overlying at least in part the bond areas 26 suitable for later attachment to the tack-bonded portions 22. Preferably, the material 28 is a hook type material suitable for attachment to loose loop type material if used for portions 22.

Figure 6:
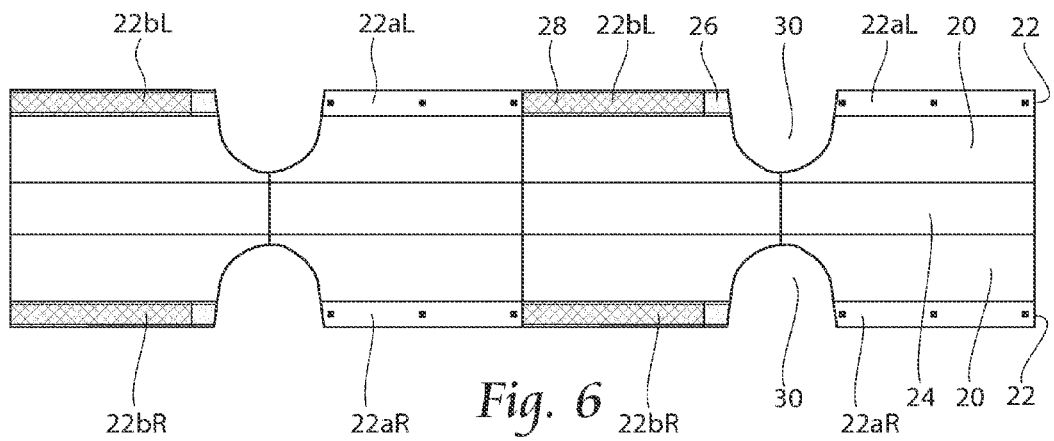
FIG. 6 is a top planar view of assembly of embodiment shown in FIG. 5, with the top and bottom non-stretch materials folded over and bonded in portions to the stretch portions, and a hook material applied to the back side panel proximate to the bond area, with portions of the assembly removed by die cut to facilitate shaping of the side panel.

Referring now to FIG. 6, the next step in the process is to die cut areas 30 from side panel assembly which can be discarded or preferably recycled. Preferably, portions 30 of the side panel assembly are removed by die cut or other means to facilitate shaping of the side panel to conform with the waist or leg openings of the diaper configuration, shaped to conform to the body of the wearer.

Figure 7:
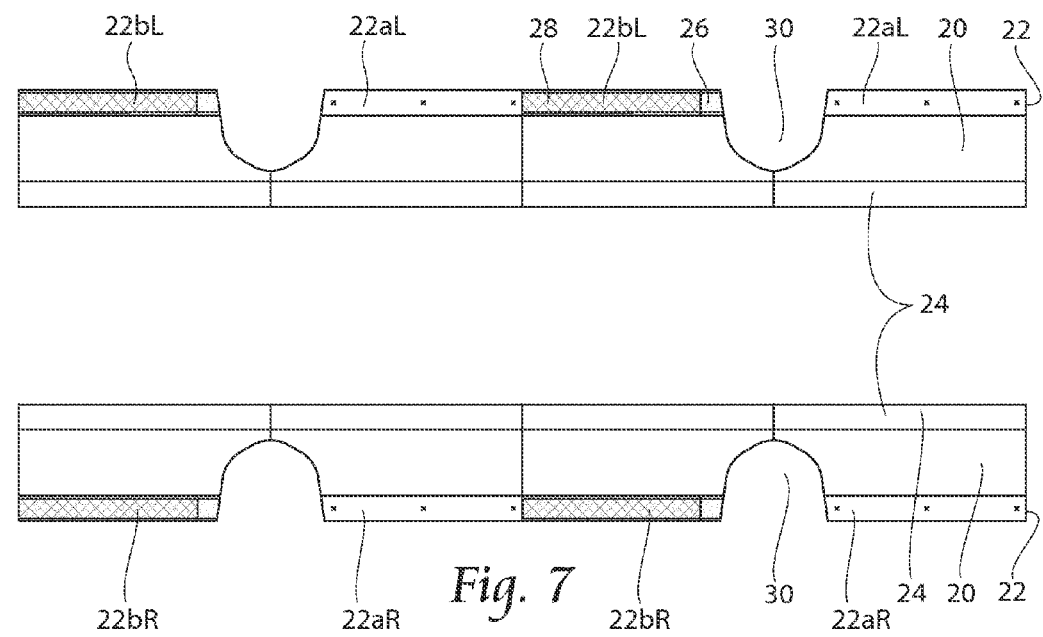
FIG. 7 is a top planar view of assembly of embodiment shown in FIG. 6, with the top and bottom non-stretch materials folded over and bonded in portions to the stretch portions, and a hook material applied to the back side panel proximate to the bond area, with portions of the assembly removed by die cut to facilitate shaping of the side panel, and the side panel slit and spread apart.

Next, as shown in FIG. 7, the side panel assemblies are slit, preferably in the middle of the non-stretch panel 24, and spread apart to increase the distance between the left side panels (22aL and 22bL) and the right side panels (22aR and 22aL) panels to form left and right intermediate assemblies. Next, the front panel (22aL and 22aR) assemblies are separated from the 22bL rear panel assemblies (22bL and 22bR) panels, for instance by slitting and slip cutting methods (not shown) for deployment onto a continuous top sheet web 12 in the positions as shown in FIG. 8.

Figure 8:
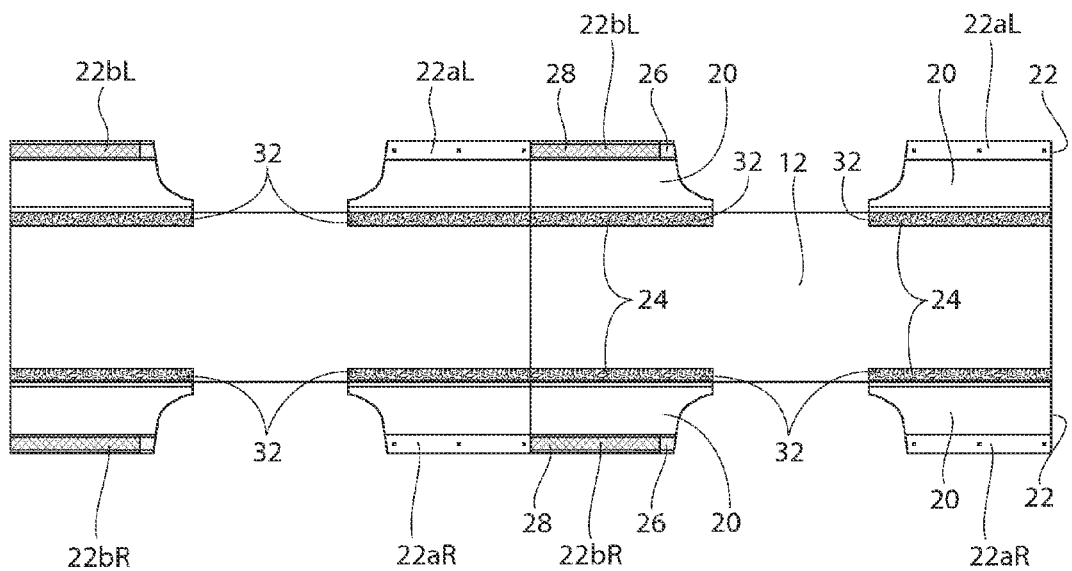
FIG. 8 is a top planar view of assembly of embodiment shown in FIG. 7, with the top and bottom non-stretch materials folded over and bonded in portions to the stretch portions, and a hook material applied to the back side panel proximate to the bond area, with portions of the assembly removed by die cut to facilitate shaping of the side panel, and the side panel slit and spread apart, bonded to a top sheet material.

As shown on FIG. 8, the non-stretch panel 24 portions of the side panel assemblies are introduced to the top sheet assembly 12 in overlapping fashion, and bonded thereto in the portions of an overlap between the non-stretch panel 24 and top sheet assembly area identified as overlap area 32.

Figure 9:
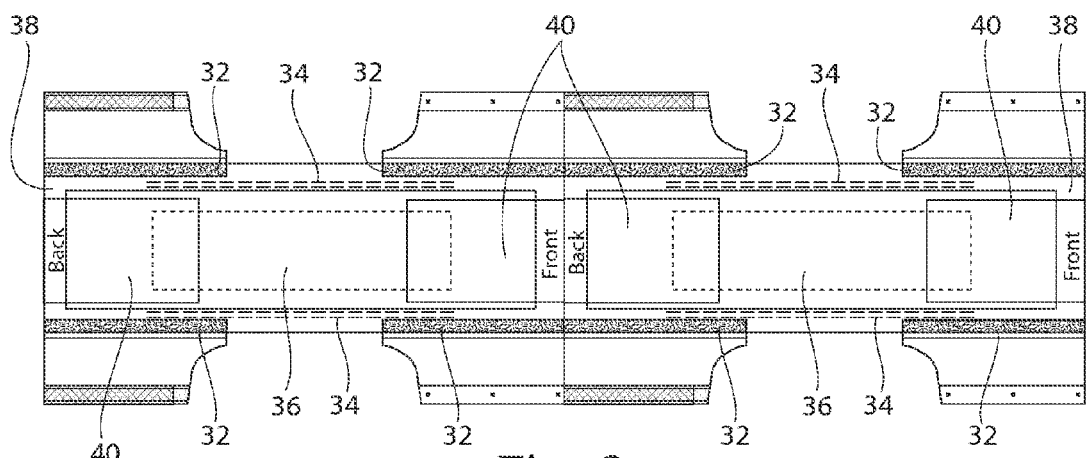
FIG. 9 is a top planar view of assembly of embodiment shown in FIG. 8, with the top and bottom non-stretch materials folded over and bonded in portions to the stretch portions, and a hook material applied to the back side panel proximate to the bond area, with portions of the assembly removed by die cut to facilitate shaping of the side panel, and the side panel slit and spread apart, bonded to a top sheet material, and this combination combined with a core and back sheet material.
Figure 12:
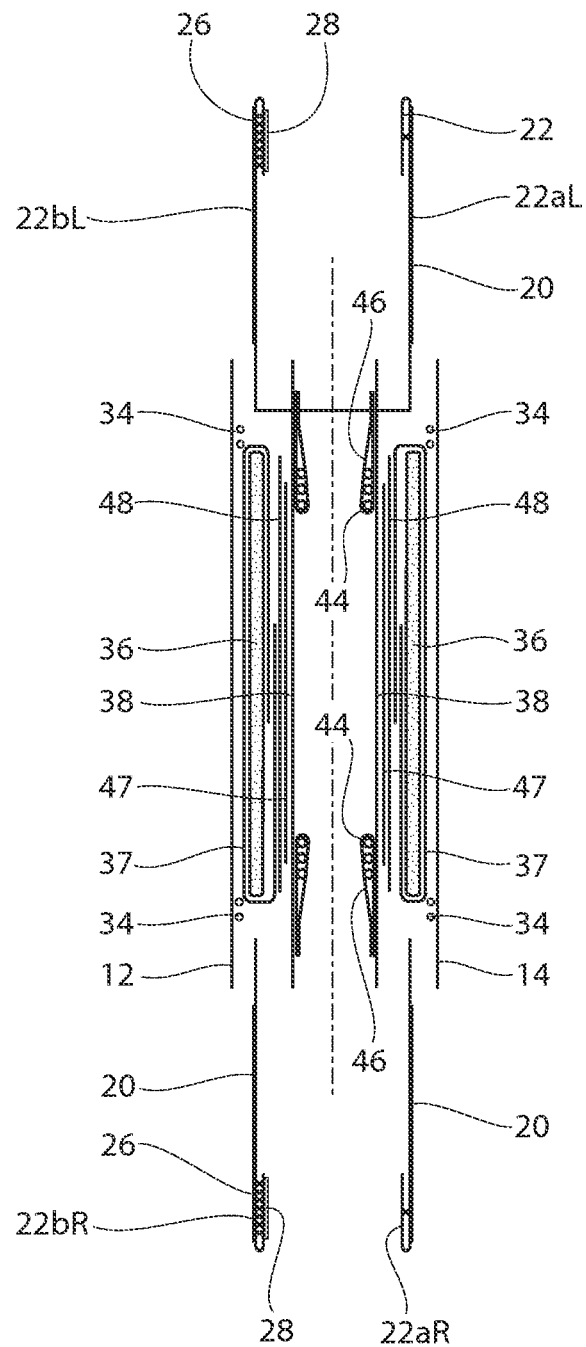
FIG. 12 is an exploded cross sectional view of the pre-fastened pull-on pant with a side lap seam formed by the methods of the present invention.

Referring to FIGS. 9 and 12 (showing the product cross-section after folding), after slitting the side panel assembly to form independent left (22aL and 22bL) and right (22aR and 22bR) panels, the left panels are further subdivided to form the left front (22aL) and left rear (22bL) panels, and to form the right front (22aR) and right rear (22bR) panels, and introduced to the back sheet material 30. At this point, as shown in FIG. 9, additional components of the diaper panel can be introduced either independently or in pre-constructed fashion. Included are the cuff non-woven 46 containing cuff elastics 44, leg elastics 34, the inner non-woven 38, the absorbent core 36 captured by tissue, the acquisition layer 47, poly layer 40, inner non-woven 38, and waist band 48.

Figure 10:
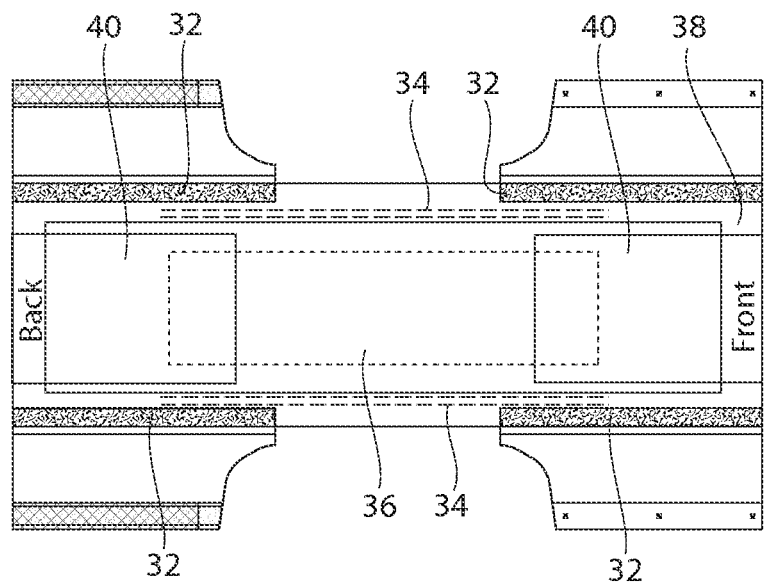
FIG. 10 is a top planar view of assembly of embodiment shown in FIG. 9, with the top and bottom non-stretch materials folded over and bonded in portions to the stretch portions, and a hook material applied to the back side panel proximate to the bond area, with portions of the assembly removed by die cut to facilitate shaping of the side panel, and the side panel slit and spread apart, bonded to a top sheet material, and this combination combined with a core and back sheet material, showing the finished product prior to folding.

Referring now to FIG. 10, two adjacent products can be separated from one another, for instance, by die cutting, to form independent products 10. FIG. 10 is a top planar view of assembly of embodiment shown in FIG. 9, with the top and bottom non-stretch materials folded over and bonded in portions to the stretch portions, and a hook material applied to the back side panel proximate to the bond area, with portions of the assembly removed by die cut to facilitate shaping of the side panel, and the side panel slit and spread apart, bonded to a top sheet material, and this combination combined with a core and back sheet material, showing the finished product prior to folding.

Figure 11:
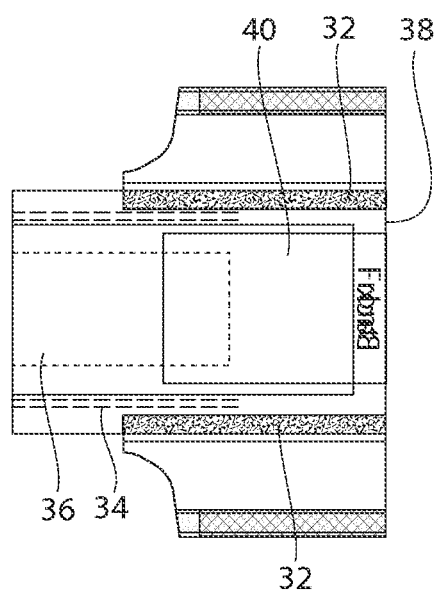
FIG. 11 is a finished product after folding, and prior to packaging.

Referring now to FIG. 11, the diaper product is folded generally at its midsection to form a folded product, with the material 28 being urged against the material 22, to form the refastenable pre-fastened product. In this fashion, the hook material 28 contained on side panel portion 22bL is joined with the side panel portion 22aL, and the hook material 28 contained on side panel portion 22bR is joined with the side panel portion 22aR. This joinder is done by pressure during the folding process, such that the finished product after folding will have pre-sealed sides. If the user desires, the hook material 28 can then be separated from the side panel portions 22aL and 22aR for taking the garment off the user if the product is insulted, or can be opened and re-sealed if the product is still clean.

Referring now to FIG. 13, a schematic representation of formation of an alternate embodiment of the present invention is shown, disclosed is a nonwoven tab process with a continuous hook 28 formation, with the hooks 28 away from the body. The formation of this product is much the same as previously described. Working from left to right on FIG. 13, in sequential fashion, non-woven tab material 22 is folded over at the top and the bottom and tack bonded. Next, hook material 28 is coupled to the tack bonded material 22, slit and spread. Next, this composite is introduced to side panel material 20. Die cut areas 30 are removed from the side panel assembly. At this point in the procedure, the construction process resumes at the point previously described with reference to FIGS. 6-11. To recap, the left and right and front and back panels are slit and separated, as shown in FIG. 7, bonded to the incoming chassis web (FIGS. 8, 9), severed into individual diapers (FIG. 10) and folded (FIG. 11) prior to packaging.

Referring now to FIG. 14, a schematic representation of formation of an alternate embodiment of the present invention is shown. In this embodiment, the hook material 28 is applied to tack bonded material 22 discretely (as opposed to continuously, as shown on FIG. 13). Discrete application of the hook material 28 can be performed, for instanced by slip/cut techniques. In this embodiment, the discrete hook material 28 is not severed, instead the combination tab 20/hook 28 material is severed in between hook 28 portions.

Figure 15:
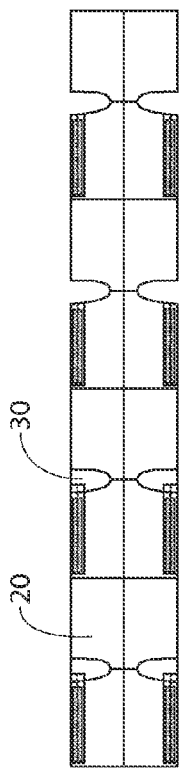
FIG. 15 is a schematic representation of formation of an alternate embodiment of the present invention, disclosed is a nonwoven tab process with a discrete hook formation extending into a die cut region, with the hooks away from the body.

Referring now to FIG. 15, an alternate embodiment of the present invention is shown, in which a nonwoven tab created of material 20 (longer than the hook material 28 segments) extend into the die cut region 30 such that in use the material 20 would extend nearly the length of the back side panel 20.

Figure 16:
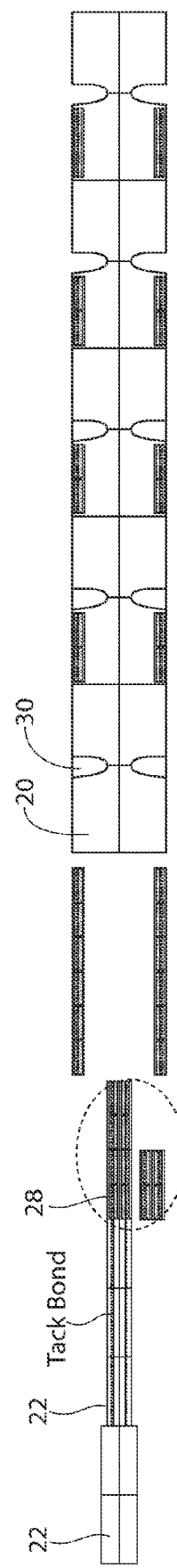
FIG. 16 is a schematic representation of formation of an alternate embodiment of the present invention, disclosed is a nonwoven tab process with a discrete hook overlapping cut formation, with the hooks away from the body.

Referring now to FIG. 16, an alternate embodiment is shown, with a discrete hook 28 overlapping the die-cut formation, with the hooks away from the body. In this embodiment, the hook material is introduced such that the hook material 28 overlaps the space where the material is cut prior to introduction onto the side panel. The result is that the hook material 28 resides on the back side panel in two discrete pieces. The same result is achieved if, as shown in FIG. 17, multiple discrete hook portions 28 are applied to the non-woven tab 20 material, slit and separated prior to introduction onto the side panels 22.

Referring now to FIG. 18, an alternate embodiment of the present invention is shown with nonwoven tab process with hooks 28 on the front side panel, with the hooks 28 facing away from the body.

Referring now to FIG. 19 an alternate embodiment of the present invention is shown, with hooks 28 on the front side panel, and the folded over nonwoven 22 on the back panel, with hooks 28 toward the body. FIG. 20 is similar, except that the folded over nonwoven 22 is on the front panel, and the hooks 28 are on the back panel.

Figure 21:
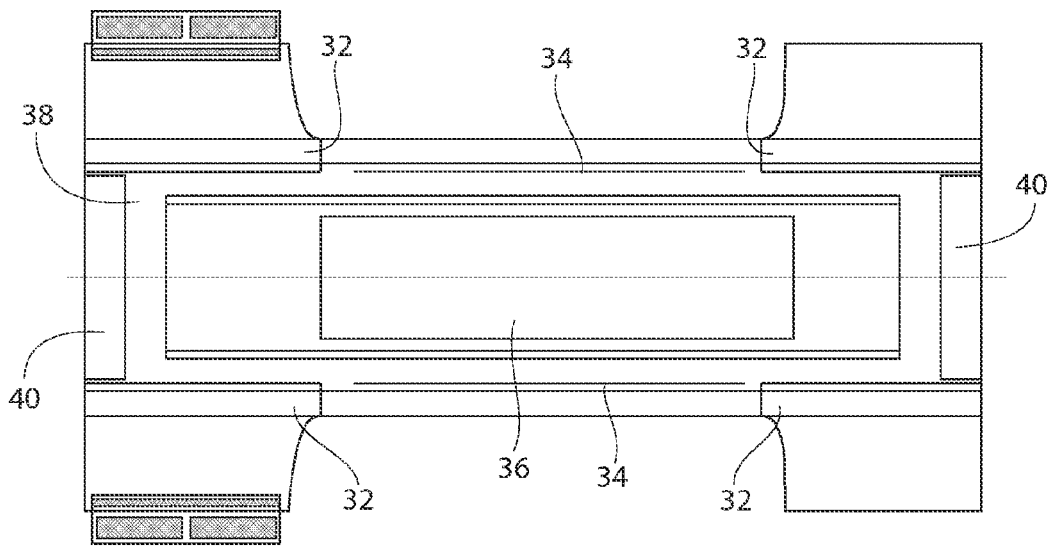
FIG. 21 is a plan view of a product produced according to the present invention.
Figure 22:
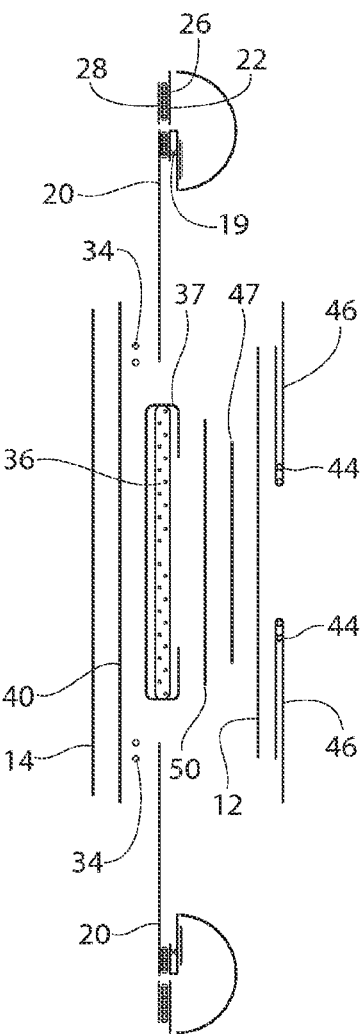
FIGS. 22-24 are cross sectional views of a product produced according to the present invention.
Figure 23:
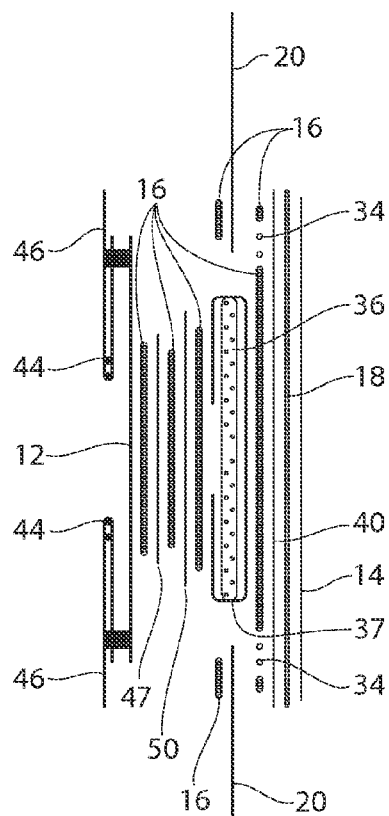
Figure 24:
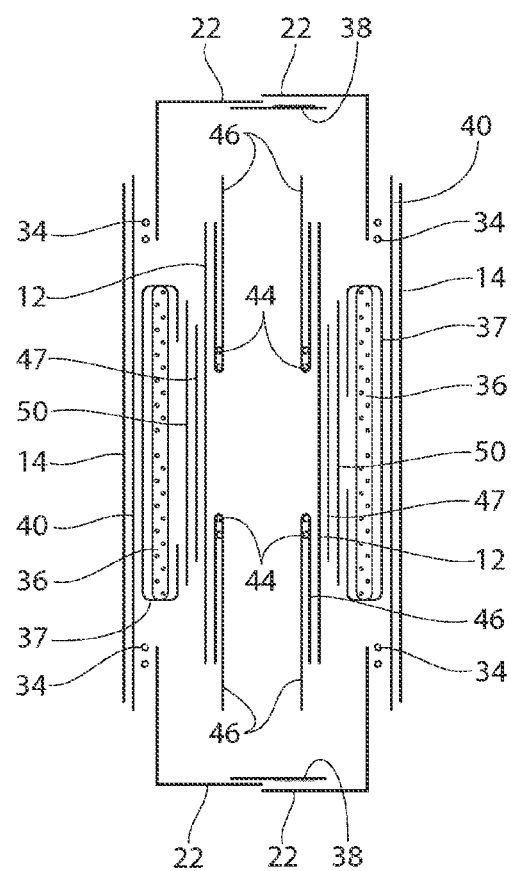

Referring now to FIG. 21 is a plan view of a product produced according to the present invention, is shown, with a back side panel cross section shown in FIG. 22, a front side panel construction shown in FIG. 23, and a lap-seam full product cross section shown in FIG. 24. Referring to FIG. 22 showing the back panel cross section, undergarment 10 is formed with top sheet 12, back sheet 14, bonded where desired with adhesive 16 or ultrasonic bonds 18, or tack bonds 19. A poly layer 40 is provided, as are leg elastics 34, panels 20, absorbent core 35 carried by core wrap 37 (preferably non-woven), top tissue 50, acquisition layer 47, and cuff elastics 44 carried by cuff non-woven 46.

Referring to FIG. 23 showing the front panel cross section, the top sheet 12 is coupled to the cuff 46, and the acquisition layer 47, the top tissue 50, and next the ftong panels about the core 36 carried by the core wrap 37. Leg elastics 34 are provided, and completing the cross section is poly 40 coupled to the back sheet 14.

FIG. 24 shows the lap seam (overlap) provided by the hook material 38, releasably coupled about the waist of a user with material 22.

The foregoing is considered as illustrative only of the principles of the invention. Furthermore, since numerous modifications and changes will readily occur to those skilled in the art, it is not desired to limit the invention to the exact construction and operation shown and described. While the preferred embodiments have been described, the details may be changed without departing from the invention, which is defined by the claims.

I claim:

1. A method of forming a resealable pant, the method comprising:
    providing a first running web of tab material;
    folding over said first web at a top and a bottom of said web to create top and bottom folded over portions of said first web, and tack bonding said folded over portions of said first web to said first running web;
    providing a hook material to said first running web of tab material to thereby form a folded over composite material, said hook material coupled to said folded over portion of said first web in discrete segments;
    slitting and spreading said composite material;
    providing a web of side panel material;
    coupling said folded over composite material to said web of side panel material;
    dividing said side panel material into a right side and a left side, and a front side and a back side, to create a front right panel, a front left panel, a back right panel and a back left panel,
    coupling said front right panel and said back right panel to a chassis web in a spaced apart relationship;
    coupling said front left panel and said back left panel to said chassis web in a spaced apart relationship;
    cutting at least one of said discrete segments of hook material to create at least two hook portions on each of said back left panel and back right panel;
    severing said chassis web to form a pant comprising said front side panel material and said back side panel material; and
    folding said pant to join said front side panel material and said back side panel material with said hook material to thereby form a resealable side lap seam.

* * * * *